United States Patent [19]

Morton

[11] Patent Number: 5,791,350
[45] Date of Patent: Aug. 11, 1998

[54] DEVICE AND METHOD FOR MEASURING FORCE SYSTEMS

[76] Inventor: John Y. Morton, 239 Old Farms Rd., Avon, Conn. 06001

[21] Appl. No.: 482,611

[22] Filed: Jun. 7, 1995

[51] Int. Cl.⁶ .................................................. A61B 5/103
[52] U.S. Cl. ........................ 128/777; 128/774; 73/862.53
[58] Field of Search ........................ 128/774, 782, 128/781, 776, 777; 73/862.45, 862.53, 862.473, 862.474, 862.451, 781, 782

[56] References Cited

U.S. PATENT DOCUMENTS

| | | | |
|---|---|---|---|
| 3,307,393 | 3/1967 | Kessler | 73/781 |
| 3,341,795 | 9/1967 | Newman et al. | 73/781 |
| 3,648,514 | 3/1972 | Vilain | 73/781 |
| 4,493,220 | 1/1985 | Carignan et al. | 73/862.66 |
| 4,701,660 | 10/1987 | Baumgartner et al. | 73/781 |
| 4,742,832 | 5/1988 | Kauffmann et al. | 128/774 |
| 5,060,525 | 10/1991 | Hafner | 73/862.54 |
| 5,125,270 | 6/1992 | Kovacevic | 128/774 |
| 5,125,408 | 6/1992 | Basser | 128/774 |
| 5,213,112 | 5/1993 | Niwa et al. | 128/774 |
| 5,216,817 | 6/1993 | Misevich et al. | 128/774 |
| 5,224,469 | 7/1993 | Mocny | 128/55 |
| 5,289,826 | 3/1994 | Kovacevic | 128/774 |
| 5,360,016 | 11/1994 | Kovacevic | 128/774 |
| 5,396,887 | 3/1995 | Imran | 128/774 |
| 5,400,661 | 3/1995 | Cook et al. | 73/862.043 |
| 5,425,775 | 6/1995 | Kovacevic et al. | 128/774 |
| 5,471,996 | 12/1995 | Boatright et al. | 128/774 |

*Primary Examiner*—Jeffrey A. Schmidt
*Assistant Examiner*—Patrick W. Rasche
*Attorney, Agent, or Firm*—Daren C. Davis

[57] ABSTRACT

A device and method for measuring force systems is provided. The device measures and displays one or more components of a force system generated by medical or dental appliances or body tissues. The invention provides a probe or attachment device for engaging the structure to be measured, such as orthodontic springs, wires, and appliances; surgical fixation devices; and body tissue. The probe transmits the force system produced by the structure to a sensor bar which is attached to the probe. The sensor bar resolves the force system being measured into electrical signals. A device is used to display representations of the electrical signals.

21 Claims, 6 Drawing Sheets

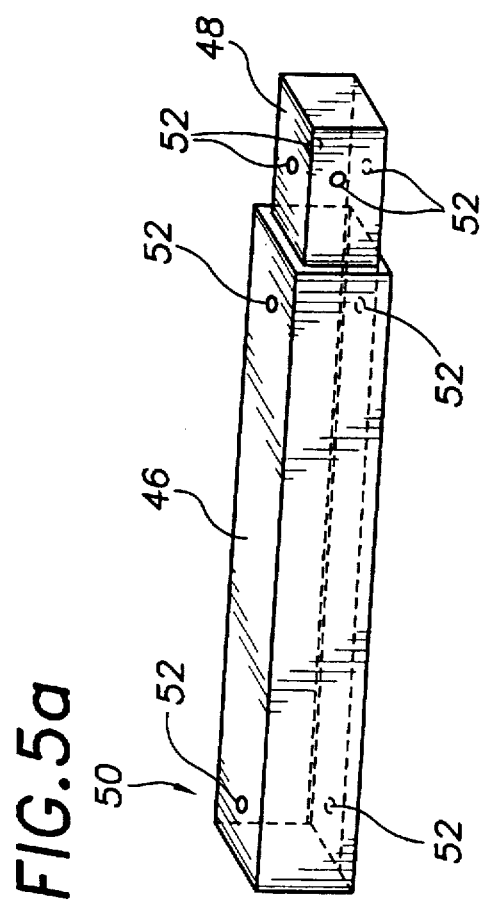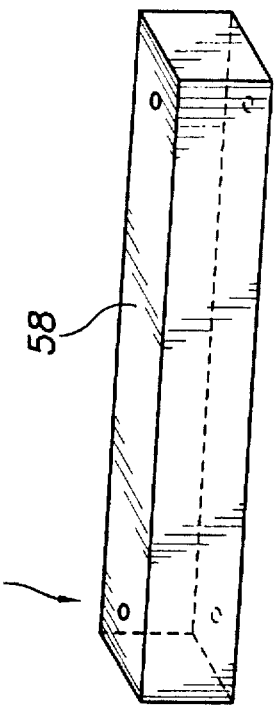

5,791,350

DEVICE AND METHOD FOR MEASURING FORCE SYSTEMS

This invention was made with Government support under Grant No. R44 DE10014 awarded by the National Institutes of Health. The Government has certain rights to this invention.

TECHNICAL FIELD OF THE INVENTION

The invention relates generally to a device and method for measuring and displaying force systems, and more particularly to a device and method for measuring and displaying force systems generated by medical or dental appliances or body tissues.

BACKGROUND OF THE INVENTION

A goal of orthodontic treatment is to reposition teeth to a location which affords improved function and improved aesthetics. To accomplish tooth movement, orthodontic springs, wires, and appliances are used to apply a force system to a tooth which initiates a biological response from the tissues which support the tooth. Bone surrounding the tooth is selectively destroyed and reconstructed, effectively displacing the tooth to a new location.

Research emphasis has been placed on determining the force system which must be applied to the tooth to accomplish a desired tooth movement and developing the methods for fabricating a spring or appliance which will produce that force system. However, the research equipment capable of measuring these force systems are physically large and unsuitable for applications beyond a research laboratory. It is desirable to have instrumentation which can be sterilized, is small in size, and is portable in nature.

A force system is a group of forces and/or couples arising from the action of one body on another and includes the moments of the individual forces about an axis or point, and the moments of the couple. A force is the action of one body on another. The moment of a force about a point is the product of the force and the perpendicular distance from the point to the line of action of the force. It is a measure of the tendency of the force to produce a rotation of the body. Two parallel forces of equal magnitude which act in opposite directions and are not collinear form a couple. The moment of a couple is the product of the magnitude of one of the forces and the perpendicular distance between the lines of action of the forces. It is an indication of the tendency of the couple to produce a rotation of the body. Orthodontic appliances are capable of producing forces in all three principal directions, and further, may produce moments and couples about the three principal axes. There exists a need to have instrumentation which simultaneously measures a plurality of components of a force system available to those performing orthodontic procedures. Application of incorrect force systems may produce undesirable tooth movement which must be corrected, thereby prolonging treatment time. Application of high force or couple magnitudes can result in tissue damage, root resorption, hyalinization, bone loss, and patient discomfort and pain. Improper preactivation of an appliance, or over-activating, over-stretching, or over-twisting of an appliance may result in material fatigue or failure of the appliance.

The present invention has been developed to provide the method and means to measure and control the force system produced by an appliance or wire, and further, to provide the method and means to prescribe, calibrate, and deliver an accurate force system.

Similar problems exist in other medical fields. In oral surgery, orthopaedics, and veterinary medicine, application of improper force and/or moment magnitudes during procedures such as installation of fixation devices, such as screws or pins, can result in malunion of fractures, delay of healing, fracturing of the bone, or loss of pitch. Unwanted fixation screw movements, such as translations and rotations, are reduced and functionality improved when insertion couples are maximized for a particular bone specimen. However, in the attempt to apply the greatest possible insertion moment, the bone is often damaged. The problem most often encountered during insertion of a screw at surgery is stripping the bone threads when working with thin cortical bone. The invention is developed to improve fixation performance by providing a means to calibrate and monitor moments required for insertion, and in so doing, reduce the occurrence of bone thread failure.

OBJECTS OF THE INVENTION

One object of the invention is to provide a device and method for measuring force systems.

Another object is to provide a device and method for measuring force systems produced by orthodontic springs, wires, and appliances.

Still another object is to provide a device and method for calibrating or activating an orthodontic appliance prior to inserting it into the oral cavity.

Yet another object of the invention is to provide a device and method for measuring the force systems developed during the installation of surgical fixation devices.

A further object of the invention is to provide a device and method for measuring force systems produced by body tissue.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

According to the present invention, the foregoing and other objects are attained by providing a device and method to measure and display one or more components of a force system generated by medical or dental appliances or body tissues. The invention provides a probe or attachment device for engaging the structure to be measured, such as, orthodontic springs, wires, and appliances; surgical fixation devices and wires; and body tissue. The probe transmits the force system produced by the structure to a sensor bar which is attached to the probe. The sensor bar resolves the force system being measured into electrical signals. A device is used to display representations of the electrical signals.

In accordance with another aspect of the invention, the sensor bar is comprised of a beam. The beam has several strain gages attached to the beam for resolving the force system being measured into electrical signals.

In yet another aspect of the invention, the sensor bar is made of a large tube which has a bore extending along its major or longitudinal axis. A smaller tube is partially contained within the bore of the larger tube, with the major axis of the smaller tube aligned with the major axis of the larger tube. Strain gages which are used to measure force are placed at opposite ends on the larger tube. The strain gages which are used to measure couples are placed on the smaller dimension tubing.

Another aspect of the invention provides a method of measuring a force system by engaging an orthodontic device or body tissue with a probe is provided. The force system is transmitted from the device or tissue to the probe and converted into electrical signals. Representations of the electrical signals are then displayed.

In yet another aspect of the invention, a method of measuring a force system by engaging a surgical fixation device, such as a screw or pin, with a probe is provided. The force system is transmitted from the device to the probe and converted into electrical signals. Representations of the electrical signals are then displayed.

As can be readily seen by these aspects of the invention, the device and method for measuring force systems provides a useful, compact instrument for measuring forces and couples generated by a variety of structures.

BRIEF DESCRIPTION OF THE DRAWINGS

FIG. 5 is a side sectional view of the probe of the present invention engaging a surgical fixation device.

BEST MODE FOR PRACTICING THE INVENTION

A force system applied to the end of a probe is transmitted to a sensor bar. The force system acting on the sensor bar produces a pattern of strains on the surface of the sensor bar. Strain gages bonded to the surface of the sensor bar at locations which maximize their sensitivity to the force system component to be measured are connected in an electronic circuit. This circuit produces a signal proportional to one component of the force system, either a force or a moment. This signal is conditioned and the magnitude of the force system component is displayed. One embodiment measures two forces at right angles to one another and displays each force magnitude on separate displays. Another embodiment measures the moment produced by the forces and couples and one force and displays magnitudes of both the force and the couple on two displays. Other embodiments which measure other combinations of the force system are readily apparent and included in this invention.

Figure 1:
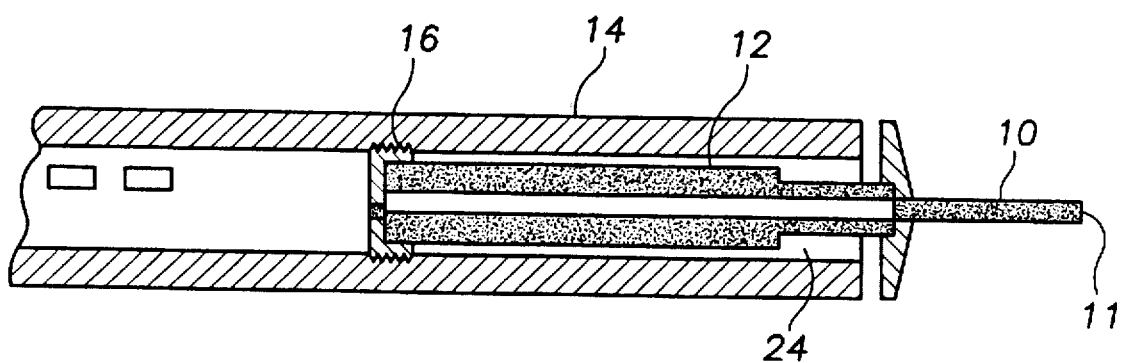
FIG. 1 is a side sectional view of the force system measuring instrument of the present invention.

Referring now to FIG. 1, a probe 10 is used to enter the body cavity, contact the appliance or tissue, and transmit the force system imparted to the probe 10 by the appliance or tissue at the point of origin to the sensor bar 12 and electronic circuitry (not shown) which remain outside the body cavity. The probe 10 can be any convenient means to attach the sensor bar 12 to the appliance or tissue to be measured. A probe 10 of any length necessary to allow entry into the body cavity and provide access to the appliance or tissue to be measured may be used without affecting the accuracy of the device. The probe 10 comes into contact with body tissue and fluids, hence it is composed of one or more materials which are biocompatible and heat sterilizable, such as stainless steel.

At tip 11 of the probe 10 there is one of several mechanisms for engaging a medical or dental appliance or body tissue. A simple rod, as shown by probe 10, can be used as a contact probe. Any appliance or tissue coming into contact with the probe 10 will impart a force system to the probe 10 which is in turn transmitted to the sensor bar 12 and measured.

The support post 16 is threaded on its exterior. The housing 14 is internally threaded and attaches to the support post. In one embodiment, two areas are machined flat on the housing 14 to ensure proper orientation when the instrument is fixed in a vice, an arrangement which is favorable for benchtop measuring of force systems produced by appliances.

A stop is machined into the housing to ensure against over deflecting the sensor bar which would result in failure of the strain gages.

Figure 2A:
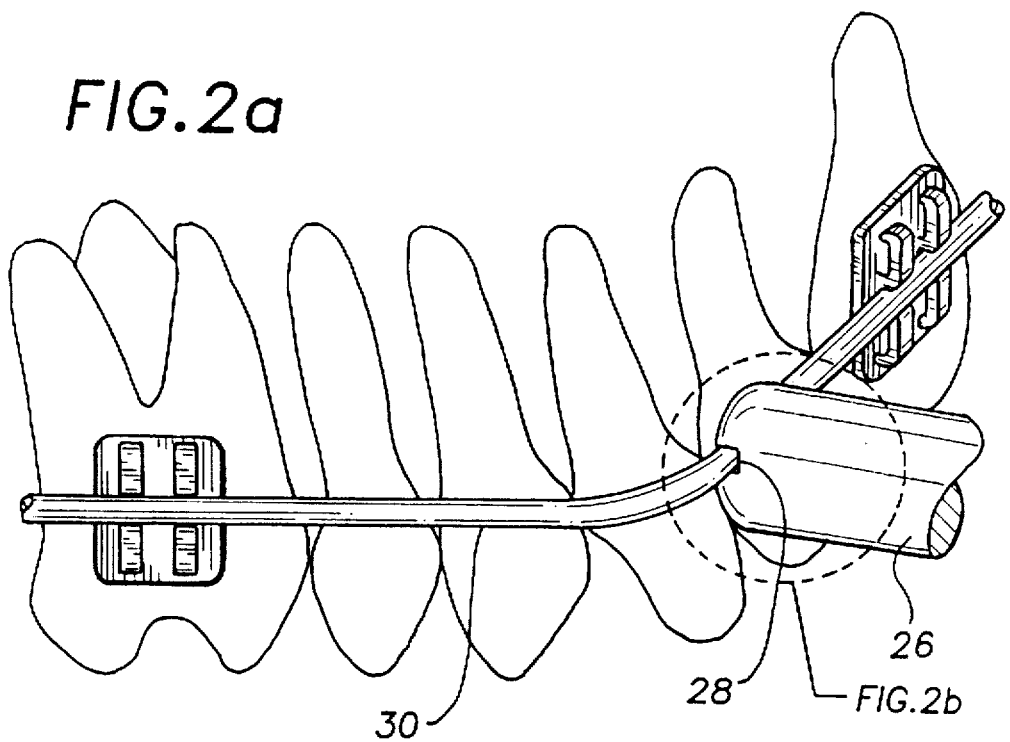
FIG. 2 is a schematic block diagram of the power supply, sensor bar, circuitry, and display of the present invention.
Figure 2B:
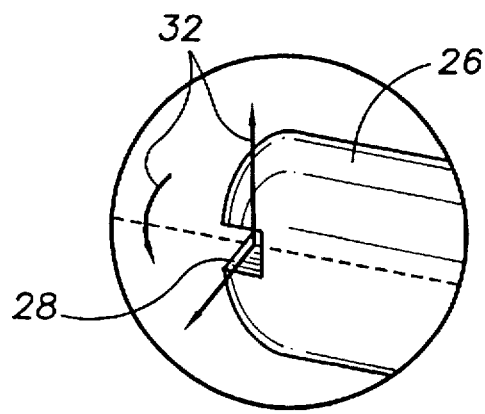

As can be seen in FIGS. 2a and 2b, a probe with a ground or milled slot 28 allows engagement of an orthodontic archwire 30 or spring. By simply substituting the probe slot 28 in place of the orthodontic bracket slot or tube, the force system 32 acting on the bracket is imparted on the probe 26 and measured. To accurately measure the force system which is produced in each orthodontic circumstance, the probe 26 must be manipulated to hold the wire 30 in the same orientation as when the wire 30 is engaged in the appliance bracket slot or tube. The more accurately the step and angular relationships between the bracket and wire 30 are reproduced with the probe 26, the more accurate the force and moment measurements will be. If the wire 30 is not to be engaged in a slot 28, placing the probe 26 at the point of contact will result in an accurate force system being applied to the probe 26. Also, should the situation allow, the probe 26 can be used to engage the wire 30 in the slot or tube, and a force system 32 measurement taken just prior to engagement. A clamping mechanism (not shown) may be used to restrain the appliance or tissue at the probe tip and allow the appliance or tissue to be stretched, twisted, activated, or manipulated while measurements of the force system are taken.

Figure 3:
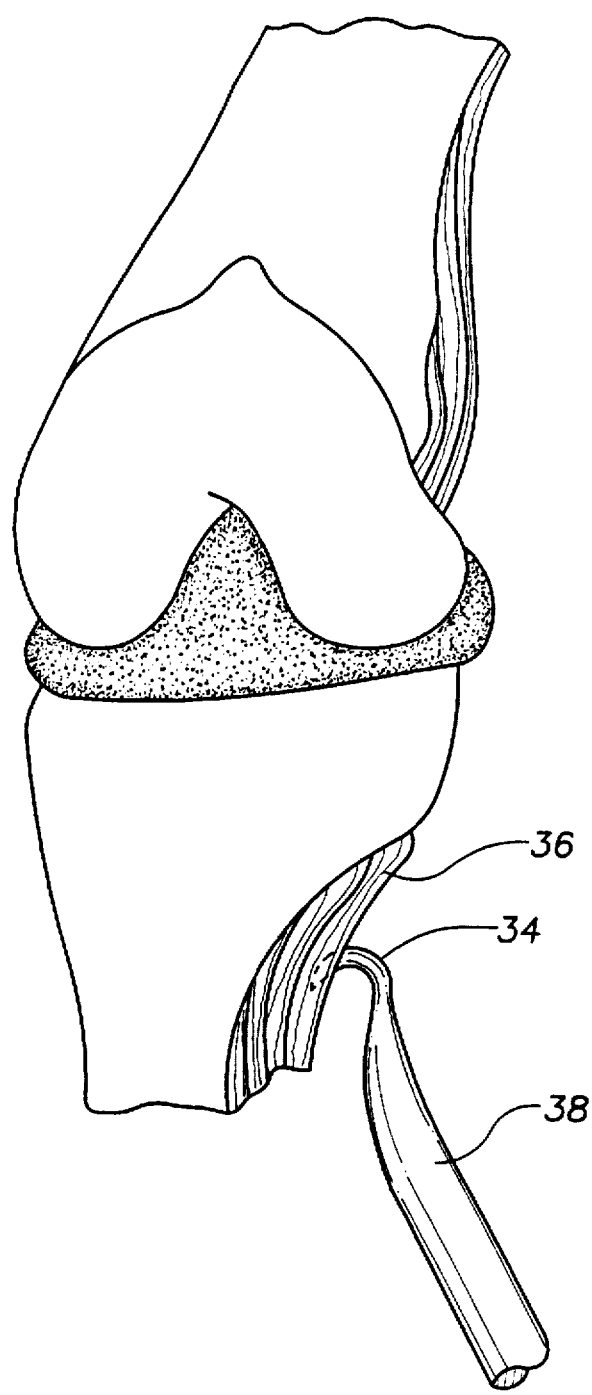
FIGS. 3a and 3b are perspective views of sensor bars of the present invention.

Referring now to FIG. 3, a clamp (not shown) or hook 34 can be used to restrain a tendon, ligament, or other tissue 36 for medical procedures, and the user can displace or rotate the instrument and monitor the force system which results.

A hook 34 at the end of the probe 38 can also be used to engage elastics and straps so that measurements of activation forces can be taken. Measurement of the horizontal and vertical force components produced by orthodontic headgear allows determination of the resulting applied force direction and magnitude.

A probe with two pins located a finite distance apart can be used to span over a bracket or used to rotate or displace a wire. The force system components imparted to the probe can then be measured. This type of probe is particularly useful in measuring force systems produced by appliances which undergo large deflections or rotations during the activation procedure.

Figure 4:
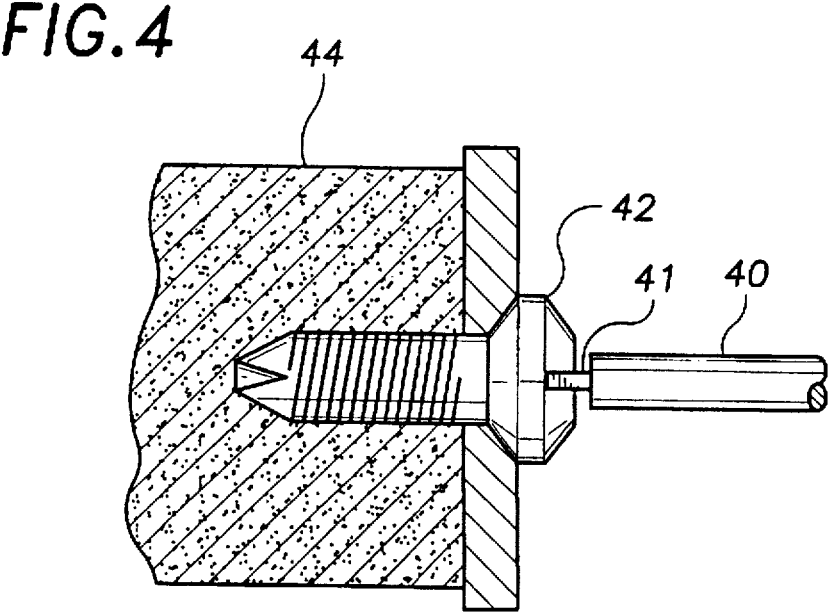
FIG. 4a is a perspective view of the probe of the present invention engaging an orthodontic device which is attached to a representative grouping of teeth.
FIG. 4b is a perspective view of the tip of the probe, enlarged to show detail.

For medical procedures, a probe 40 with a screwdriver tip 41, socket tip, or other tip configurations can be used to engage surgical fixation devices, such as fastener pins and screws 42, in bone material 44, as seen in FIG. 4. With the use of the measuring instrument of the present invention, the force and moment magnitudes can be monitored during installation of the fastener pins or screws 42 and the installation halted at a predetermined magnitude, before the surrounding tissues and/or bone 44 is damaged.

The probe can be connected to the sensor bar by any suitable means. To address hygienic concerns the entire instrument except for the probe can be covered with a disposable barrier. This tubular sheath can be placed on the instrument before each use. It can be held in place by the tapered edge of the interconnection mechanism. A small hole in the sheath is provided to allow access to connect the probe to the sensor bar.

Referring now to FIGS. 5a and 5b, since the strains produced by forces and couples can differ in magnitudes by a factor of 1,000, different sized sensor bar beams are sometimes required. In one embodiment, the sensor bar 50 is made of two pieces of telescopic tubing, the smaller tubing 48 extending beyond the larger 46. Both tubes are inserted and soldered into a square broached way in the support post 16 (FIG. 1). The tubes are soldered at the terminating ends of the larger tube 46. The strain gages 52 which are used to measure force are placed at opposite ends on the larger dimension tubing 46. A passageway allows passage of the wires from the strain gages 52 to the signal processing circuitry (not shown).

In another embodiment which would handle larger force loads, the sensor bar 56 can be made of one solid beam 58 of constant cross section. The wires from the strain gages 52 are connected to the circuitry (not shown).

Figure 6:
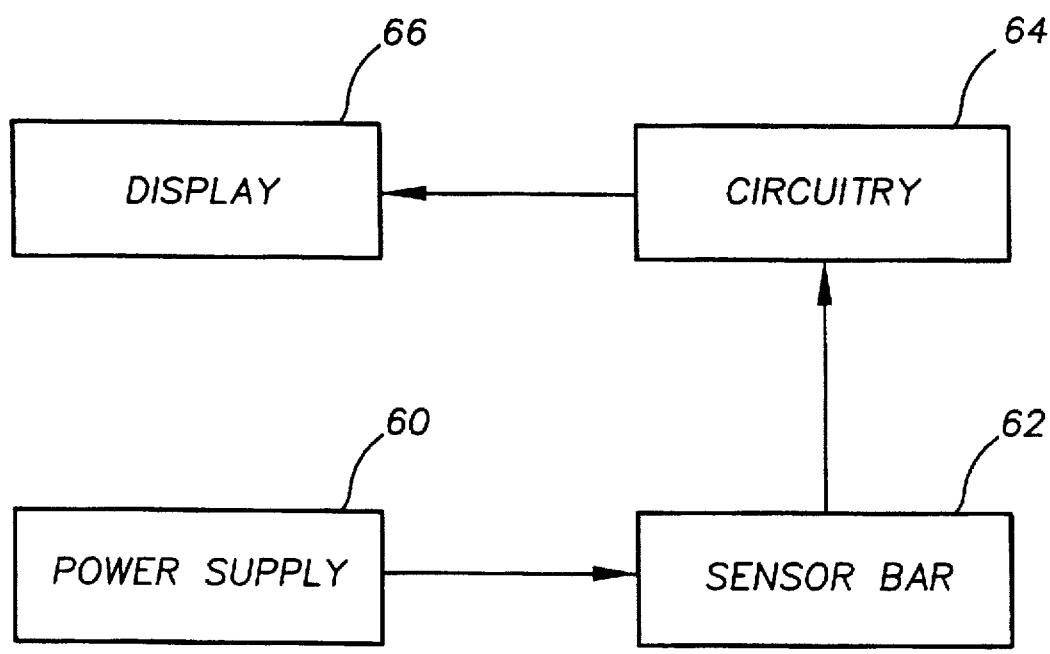
FIG. 6 is a perspective view of the probe of the present invention engaging body tissue.

As can be readily seen in FIG. 6, power is supplied by a power supply 60 to the sensor bar 62. Electrical signals from the sensor bar 62 are processed by circuitry 64 and shown on display 66. In one embodiment, power is supplied by a rechargeable battery, although replaceable batteries or an individual power supply can be used. The signal from the strain gage circuits is processed by an analog to digital converter and the magnitude of the measurement are displayed. One embodiment allows measurements of −700 to 700 grams force (g) and −4,000 to 4,000 gram-millimeter (gmm) couples. Other embodiment can allow measurements of −45 to 45 kilograms (Kg) force and −20 to 20 Newton-meters (Nm). Measuring accuracy for the device in one embodiment is ±0.1 gram force and ±1 gram-millimeter couple. Test data from one embodiment showing applied or control forces and couples and the resulting measured forces and moments and standard deviations are provided in Table 1.

TABLE 1

| Applied Deadweight | Measured Force (g) | | Applied Couple | Measured Couple (gmm) | |
|---|---|---|---|---|---|
| Force (g) | Mean | SD | (gmm) | Mean | SD |
| 10 | 11 | 1 | 500 | 488 | 7 |
| 20 | 20 | 0 | 1000 | 957 | 3 |
| 50 | 51 | 1 | 1500 | 1508 | 21 |
| 100 | 102 | 0 | 2000 | 1986 | 7 |
| 150 | 152 | 1 | 2500 | 2505 | 23 |
| 200 | 203 | 0 | 3000 | 3019 | 4 |
| 250 | 253 | 1 | 3500 | 3463 | 26 |
| 300 | 303 | 1 | 4000 | 3959 | 6 |
| 350 | 353 | 1 | | | |
| 400 | 401 | 1 | | | |
| 450 | 450 | 1 | | | |
| 500 | 496 | 0 | | | |

In summary, the present invention provides a novel device and method for measuring force systems generated by medical and dental appliances, and body tissue. Although the present invention has been described with reference to preferred embodiments, those skilled in the art will recognize that changes may be made in form and detail without departing from the spirit and scope of the invention.

I claim:

1. A force system measuring instrument comprising:
   a probe adapted to transmit said force system;
   sensor means for resolving said force system into electrical signals proportional to components of said force system, said force system comprised of more than one component, said sensor means attached to said probe;
   means for displaying representations of said electrical signals.

2. The force system measuring instrument of claim 1 wherein components of said force system are measured simultaneously.

3. The force system measuring instrument of claim 1 wherein said probe further comprises a mechanism adapted to contact a structure carrying a force system.

4. The force system measuring instrument of claim 3 wherein said structure is an orthodontic device.

5. The force system measuring instrument of claim 3 wherein said structure is animal tissue.

6. The force system measuring instrument of claim 3 wherein said structure is a surgical fixation device.

7. The force system measuring instrument of claim 1 wherein said instrument has an ability to measure force systems with a range of forces of ±45 Kg and a range of moments of ±20 Nm.

8. The force system measuring instrument of claim 1 wherein said instrument has an ability to measure force systems with a range of forces of ±600 g and a range of moments of ±4000 gmm.

9. The force system measuring instrument of claim 1 wherein said instrument has an ability to measure force systems with a range of forces of ±2 Kg and a range of couples of ±6000 gmm.

10. The force system measuring instrument of claim 1 wherein said instrument has a measuring accuracy of ±1 g of force and ±10 gmm couple.

11. The force system measuring instrument of claim 1 wherein said instrument has a measuring accuracy of ±0.1 g of force and ±1 gmm couple.

12. The force system measuring instrument of claim 1, said sensor means comprising:
   a beam;
   a plurality of strain gages fixably attached to said beam, said strain gages adapted to resolve said force system into electrical signals;
   wherein said strain gages are resistive strain gages.

13. The force system measuring instrument of claim 1, said sensor means comprising:
   a beam;
   a plurality of strain gages fixably attached to said beam, said strain gages adapted to resolve said force system into electrical signals;
   wherein said strain gages are piezoresistive strain gages.

14. The force system measuring instrument of claim 1, said sensor means comprising:
   a large tube, said large tube having a bore and a major axis, said bore aligned along the major axis of said large tube;
   a small tube, said small tube coaxially aligned with said bore of said large tube and partially contained within said bore of said large tube;

a plurality of strain gages fixably attached to said large tube and said small tube, said strain gages adapted to resolve said force system into electrical signals.

15. The force system measuring instrument of claim 14 wherein said strain gages attached to said large tube are adapted to measure forces and said strain gages attached to said small tube are adapted to measure couples.

16. The force system measuring instrument of claim 1 wherein said sensor means is removably attached to said probe.

17. The force system measuring instrument of claim 1 wherein said probe is adapted for use within an animal body.

18. The force system measuring instrument of claim 1 wherein said sensor means comprises a sensor bar adapted to resolve said force system into electrical signals corresponding to the strain due to bending in said sensor bar.

19. A force system measuring instrument comprising a probe, said probe having a base and a tip, said tip adapted to contact an orthodontic device;

sensor means for resolving said force system into electrical signals proportional to components of said force system, said force system comprised of more than one component, said sensor means having a first end and a second end, said first end attached to said base of said probe, said sensor means further comprising a beam and a plurality of strain gages fixably attached to said beam, said strain gages adapted to resolve said force system into electrical signals;

a housing, said housing having a cavity therein, said housing having a support, said second end of said sensor means attached to said support, said sensor means contained within said housing;

a display adapted to display representations of said electrical signals;

means for electrically connecting said strain gages with said display and for providing said strain gages with electrical power.

20. The force system measuring instrument of claim 19 further comprising:

a sheath adapted to protect said sensor means from contamination, said sheath having portions defining a hole, said probe extending through said hole.

21. A force system measuring instrument comprising:

probe means for transmitting said force system;

sensor means for resolving said force system into electrical signals proportional to components of said force system, said force system comprised of at least one moment component, said sensor means attached to said probe;

means for displaying representations of said electrical signals.

* * * * *